United States Patent [19]
Grubbs

[11] Patent Number: 5,575,647
[45] Date of Patent: Nov. 19, 1996

[54] GENERAL PURPOSE DENTAL HANDPIECE

[76] Inventor: Kenneth Grubbs, Rte. 2, Monroe, Ga. 30655

[21] Appl. No.: 489,317

[22] Filed: Jun. 12, 1995

[51] Int. Cl.$^6$ ...................................................... A61C 1/10
[52] U.S. Cl. ......................................... 433/114; 433/133
[58] Field of Search ....................................... 433/109, 114, 433/124, 130, 132, 133

[56]  References Cited

U.S. PATENT DOCUMENTS

| | | | |
|---|---|---|---|
| D. 250,662 | 12/1978 | Rieselman | 433/133 |
| 623,469 | 4/1899 | Hailer . | |
| 647,010 | 4/1900 | Marshall . | |
| 1,039,420 | 9/1912 | MacDonald . | |
| 1,333,809 | 3/1920 | Laurer et al. . | |
| 1,379,880 | 5/1921 | Seaborn . | |
| 1,621,190 | 3/1927 | Brown | 433/133 |
| 3,092,908 | 6/1963 | Flatland | 433/132 |
| 4,276,025 | 6/1981 | Strailhammer | 433/133 |
| 4,281,989 | 8/1981 | Glover et al. | 433/130 |
| 4,303,393 | 12/1981 | Gentry | 433/130 |

*Primary Examiner*—Cary E. O'Connor
*Attorney, Agent, or Firm*—Wigman, Cohen, Leitner & Myers, P.C.

[57]  ABSTRACT

A general purpose dental handpiece comprises a shank portion rigidly fixed to a nonarticulatable head portion adapted to removably support a drill burr along a burr axis disposed at an angle of 105°±2° with respect to the axis of the shank portion. The angle of orientation of the burr axis is an optimum angle for performing most routine dental procedures in contrast to the right angle orientation of conventional general purpose dental handpieces.

12 Claims, 1 Drawing Sheet

GENERAL PURPOSE DENTAL HANDPIECE

FIELD OF THE INVENTION

The present invention relates to dental handpieces and more particularly to an air-driven, high-speed general purpose dental handpiece.

BACKGROUND OF THE INVENTION

Early cable driven general purpose dental handpieces were subsequently replaced by belt and pulley driven straight handpieces that could accommodate long straight burrs or "contra-angle" attachments. The "contra-angle" attachments had a slight bend or angle at the junction of the shank and handle of the handpiece.

In all these early dental handpiece designs, the drill burr was arranged to exit the fixed head of the handpiece at a 90° angle in relation to the handpiece shank. It is believed that this 90° angle arrangement was the result of the use of intermeshing metal drive gears in the early, slower speed cable and belt driven handpieces. With the advent of the high-speed air-driven handpieces in the early 1950's, the fixed head dental handpiece continued to be manufactured with a burr axis oriented at a 90° angle to the shank of the handpiece. It has been discovered that the 90° exit angle for the burr from the fixed head of a general purpose dental handpiece is not an optimum angle for most routine dental procedures.

High-speed, air-driven dental handpieces are known which have the burr axis oriented in a fixed position at an angle other than 90°, e.g., 45° or 135°, for special applications, such as, for example, surgical applications in some third molar procedures (impacted wisdom teeth) and the like. However, such handpieces are not suitable for general purpose tooth reduction and caries removal and most other routine dental procedures.

Dental handpieces with varying drive mechanisms are also known which have angularly articulatable heads so that the burr axis can be positioned at different selected angles relative to the handpiece shank. U.S. Pat. Nos. 623,469; 647,010; 1,039,420; 1,333,809; 1,379,880; 4,281,989; and 4,303,393 are representative of such articulated head dental handpieces, both in the lower speed dental handpieces as well as in the high-speed, air-driven dental handpieces. Such handpieces have a relatively complex design incorporating several drive gears or fluid flow paths and, because of their complexity and cost, are simply not used by most dentists.

SUMMARY OF THE INVENTION

In view of the foregoing limitations of the prior art dental handpieces, it is an object of the present invention to overcome those limitations and other shortcomings of the prior art handpieces. It has been discovered according to the present invention that the optimum burr angle relative to the shank in a general purpose, high-speed, air-driven fixed head dental handpiece is in the range of about 103° to about 107°, and preferably about 105°. This angle is considered to be optimum for a general purpose, fixed head, dental handpiece because it provides ease of access not only to those areas in the oral cavity readily accessible by a 90° exit angle burr of a conventional general purpose dental handpiece, but also to those areas of the oral cavity which are not readily accessible or are difficult or awkward to access with the 90° exit angle burr.

Advantageously, the axis of the handpiece shank is disposed at a generally smaller angle to the axis of the handpiece handle than is typical for conventional general purpose dental handpieces. An angle between the axis of the shank and handle of about 2° is preferred, although greater angles are contemplated.

With the present invention, the placement of the fixed head of the handpiece so that the burr axis is aligned with and is movable along the drawlines for a crown does not cause any portion of the handpiece to encroach upon or engage either the maxillary or mandibular teeth. On the other hand, the conventional 90° burr angle fixed head handpiece encroaches upon the mandibular teeth when placed along the crown drawlines of the mandibular teeth. Such encroachment is completely eliminated by the present invention.

With the foregoing and other advantages and features of the present invention that will become hereinafter apparent, the invention may be more clearly understood upon consideration of the following detailed description of the invention, the appended claims and to the several views illustrated in the attached drawings, wherein:

DETAILED DESCRIPTION OF THE INVENTION

Figure 1:
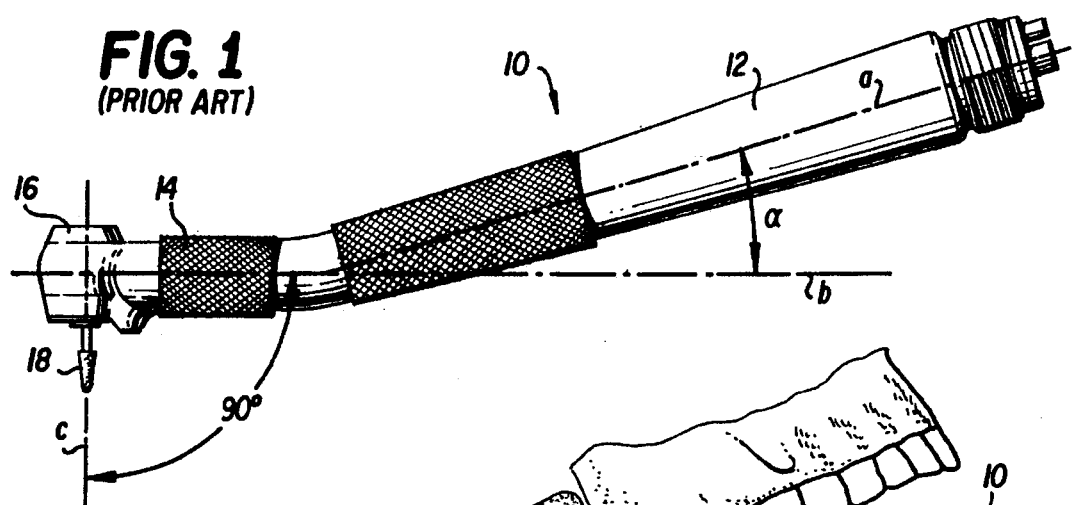
FIG. 1 is a side elevation view of a conventional fixed head, general purpose dental handpiece for a high-speed, air-driven drill burr.

Referring now in detail to the drawings, FIG. 1 illustrates a conventional prior art, general purpose, air-driven dental handpiece 10 having a handle portion 12, a shank portion 14 and a head portion 16 rigidly fixed to or integral with the shank portion 14. The axis a handle portion 12 is arranged at an angle α to the axis b of shank portion 14, typically in the range of 10° to 20°, but may be coaxial therewith, i.e., a zero angle. An air-driven burr 18 is removably mounted in fixed head 16 along an axis c which is disposed at a right angle (90°) to the axis b of shank 14. All fixed head, general purpose dental handpieces, i.e., those handpieces not intended for special procedures, are believed to have a burr axis c arranged at a right angle (90°) to the shank axis b.

Figure 2:
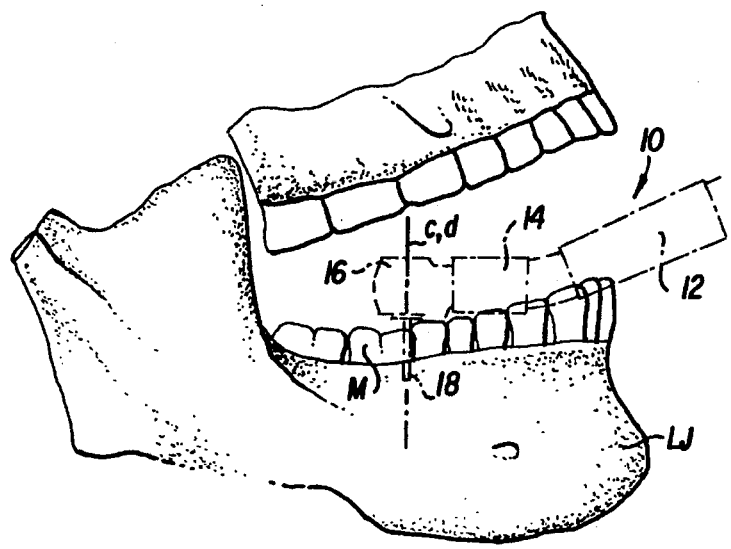
FIG. 2 is a side elevation view of the conventional dental handpiece of FIG. 1 shown in phantom lines being used in the mouth along a crown drawline of a mandibular molar.

Now referring to FIG. 2, there is shown how the burr 18 of the prior art, general purpose dental handpiece 10 is used along a crown drawline d (coincident with axis c of burr 18) of a mandibular molar M of a lower jaw LJ. As shown in phantom lines in FIG. 2, both the shank portion 14 and the handle portion 12 interfere with or encroach upon the mandibular teeth so that the axis c of burr 18 must be undesirably oriented at an angle to the optimum crown drawline d. It will be appreciated by those skilled in the dentistry art that the conventional dental handpiece 10 suffers from similar encroachments in performing other routine dental procedures.

Figure 3:
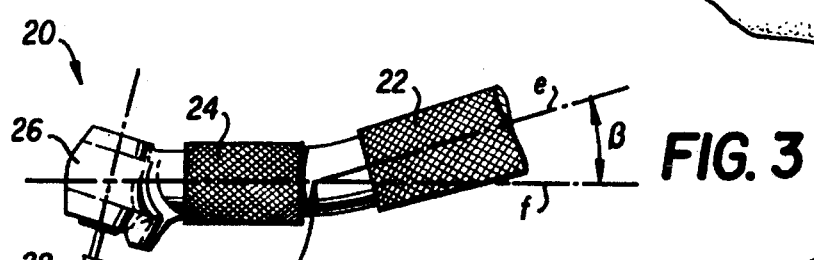
FIG. 3 is a fragmentary side elevation view of the fixed head, general purpose dental handpiece of the present invention.

Referring now to FIG. 3, there is illustrated a dental handpiece 20 constructed according to the present invention. Handpiece 20 is a general purpose, high-speed, air-driven dental handpiece that comprises a handle portion 22 (partly shown) having an axis e integrally or separately formed with a shank portion 24 having an axis f disposed at an angle β to axis e. Angle β is preferably about 2°, but may be zero or greater than 2°. A fixed head 26 is integrally formed with or rigidly affixed to shank portion 24 and removably supports an air-driven burr 28 along an axis g. Fixed head 26 is arranged with respect to shank 24 so that the axis of burr 28 is disposed at an angle of about 103° to about 107° with respect to axis f of shank 24, and preferably at an angle of 105°. This burr angle of 105° has been found to be the optimum burr angle for a fixed head, general purpose dental handpiece, is easier to use, and provides better access for most routine dental procedures than the conventional dental handpiece 10 shown in FIG. 1.

Figure 4:
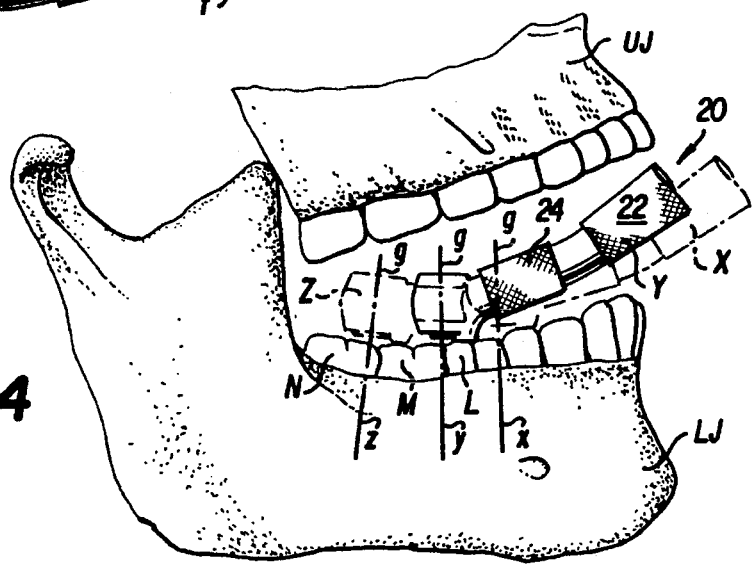
FIG. 4 is a side elevation view of the dental handpiece of FIG. 3 shown in three positions along the crown drawlines of three mandibular teeth.

Referring to FIG. 4, the dental handpiece 20 of the invention is shown in three positions X,Y,Z for the crown drawlines x, y, z of the mandibular molars L, M, N, respectively. It will also be seen in FIG. 2 that neither the handle portion 22 nor the shank portion 24 of the handpiece 20 interferes with or encroaches upon any other teeth, mandibular or maxillary, of the lower jaw LJ or the upper jaw UJ, respectively. It is this absence of interference or encroachment that makes the 105°±2° burr angle optimum for the crown procedure as well as most other routine dental procedures. Advantageously, this optimization is achieved with a fixed head dental handpiece so that no complex mechanism for angular articulation of the head portion 26 or shank portion 24 is needed. The present invention is not only applicable to air driven handpieces, but also to fluid, mechanical and electrically driven handpieces.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What I claim is:

1. A general purpose dental handpiece comprising a handle portion having a first longitudinal axis, a shank portion having a second longitudinal axis and being connected to the handle portion, a nonarticulatable head portion rigidly fixed to the shank portion, the head portion rotatably supporting a drill burr along a burr axis, said burr axis being disposed at a fixed, burr angle of about 103° to about 107° with respect to the second longitudinal axis of the shank portion, wherein said burr angle is optimum for routine dental procedures performed with a general purpose dental handpiece.

2. The dental handpiece of claim 1, wherein said angle is 105°.

3. The dental handpiece of claim 1, wherein said first longitudinal axis of the handle portion is disposed and an angle of about 2° with respect to the second longitudinal axis of the shank portion.

4. The dental handpiece of claim 1, wherein said burr is a high-speed, air-driven burr.

5. The dental handpiece of claim 1, wherein said fixed head portion and said shank portion are integrally formed in one piece.

6. The dental handpiece of claim 1, wherein said burr is removably supported in said fixed head portion.

7. A general purpose dental handpiece having a fixed, head portion integrally formed is one piece with a shank portion having a longitudinal axis, said head portion having means for supporting a drill burr along a burr axis, said burr axis being disposed at a fixed burr angle of 105°±2° with respect to the longitudinal axis of the shank portion, whereby said burr angle is optimum for routine dental procedures performed with a general purpose dental handpiece.

8. The dental handpiece of claim 7, wherein said burr is removably supported in said fixed head portion.

9. The dental handpiece of claim 7, including a handle portion affixed to said shank portion.

10. The dental handpiece of claim 9, wherein the handle portion is disposed at an angle of about 2° with respect to the shank portion.

11. The dental handpiece of claim 7, wherein said handpiece is a high-speed, air-driven handpiece.

12. The dental handpiece of claim 7, wherein the burr angle is 105°.

* * * * *